(12) United States Patent
Nakanishi et al.

(10) Patent No.: US 6,399,081 B1
(45) Date of Patent: *Jun. 4, 2002

(54) ORGANIC SILICONE RESIN POWDER

(75) Inventors: Tetsuo Nakanishi; Ichiro Ono; Shinji Miyadai, all of Gunma-Ken (JP)

(73) Assignee: Shin-Etsu Chemical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/504,949

(22) Filed: Feb. 16, 2000

(30) Foreign Application Priority Data

| Feb. 17, 1999 | (JP) | ............................................. 11-038039 |
| Feb. 18, 1999 | (JP) | ............................................. 11-039532 |
| Feb. 14, 2000 | (JP) | ......................................... 2000-034875 |

(51) Int. Cl.[7] .............................. A61K 6/00; A61K 7/00
(52) U.S. Cl. .................... 424/401; 424/489; 424/78.08; 424/78.17; 524/865; 524/866; 524/860; 524/506; 524/588; 528/32; 528/33
(58) Field of Search .................................. 424/401, 489, 424/500, 501, 78.08, 78.17; 524/865, 506, 588, 860, 866; 528/32, 33

(56) References Cited

U.S. PATENT DOCUMENTS

| 5,786,413 A | * | 7/1998 | Weidner et al. .............. 524/268 |
| 5,973,068 A | * | 10/1999 | Yamaya et al. .............. 524/865 |
| 6,153,698 A | * | 11/2000 | Kanno et al. ................ 525/125 |

* cited by examiner

*Primary Examiner*—Thurman K. Page
*Assistant Examiner*—Liliana Di Nola-Baron
(74) *Attorney, Agent, or Firm*—Millen, White, Zelano & Branigan, P.C.

(57) ABSTRACT

An organic silicone resin powder having a tabular shape the aspect ratio of which is greater than about 1 and comprising a copolymer produced by polymerization reaction between an organopolysiloxane containing at least one reactive group and at least one kind of monomer or oligomer capable of reacting to said reactive group, which can fully achieve its excellent effects when mixed in cosmetic materials, waxes and coating colors, especially in cosmetic materials.

33 Claims, No Drawings

ORGANIC SILICONE RESIN POWDER

FIELD OF THE INVENTION

The present invention relates to an organic silicone resin powder comprising a copolymer;produced by polymerization reaction between a reactive group-containing organopolysiloxane and at least one kind of monomer or oligomer capable of reacting to the reactive group, which can improve the feel of cosmetics, wax, coating color and like materials when the powder is mixed therewith, specifically which can elevate spreadability of such materials as cited above, that is, enables the materials to be applied more evenly and more thinly, and further can ensure gloss in their outward appearance.

Further, the invention is concerned with a cosmetic material which contains an organic silicone resin powder comprising a copolymer produced by the polymerization reaction between an organopolysiloxane having reactive group (s) and at least one kind of monomer or oligomer capable of reacting to the foregoing reactive group(s) to improve adhesiveness as well as impressions created by the application thereof, such as a dry feel and a feeling of refreshment, and application characteristics, such as spreadability.

BACKGROUND OF THE INVENTION

The cosmetic materials currently in use comprise a composition containing an inorganic powder, such as titanium oxide, mixed with a resin of hydrocarbon type or silicone type for the purpose of improving the characteristics required therefor and advancing such improvements. The characteristics required for cosmetic materials, as mentioned above, include pleasant feels upon application, such as a dry feel and a feeling of refreshment, spreading properties, such as even and thin application, and texture, such as gloss and color.

For instance, the cosmetic material containing a hydrocarbon type of synthetic resin powder, such as powder of polyethylene resin, polyamide resin, acrylic resin, vinyl chloride resin or epoxy resin, is disclosed in Japanese Tokkai Sho 52-99236 (the term "Tokkai" as used herein means an "unexamined published patent application").

As examples of a cosmetic material into which a resin of silicone type is compounded, mention may be made of the cosmetic material disclosed in Japanese Tokkai Hei 1-268615, which contains a powder of polyorganosilsesquioxane as a three-dimensionally cross-linked silicone, and the cosmetic material containing finely pulverized silicone rubber having elasticity as disclosed in Japanese Tokko Hei 7-53646 (the term "Tokko" as used herein means an "examined.:patent publication").

As to the inorganic powder, on the other hand, red iron oxide and titanium oxide have hitherto been used as pigment, and tabular powders, such as mica and sericite, have so far been used as an essential component of nail color, nail coat, face powder, mascara or eyeliner.

Those inorganic powders have hydroxyl groups on their surfaces, so that they are generally used after undergoing silicone, fluoropolymer, metallic soap or activator treatment for weakening their surface activity and the cohesiveness thereof or making the surfaces hydrophobic.

However, the cosmetic materials containing the hydrocarbon type of synthetic resins as recited above are generally apt to have high hardness, and so the application thereof occasionally arises a uncomfortable feeling, such as a hard feel, in the users.

On the other hand, the cosmetic materials containing finely pulverized silicone rubber can wipe away a hard feel, but they are not easy to handle because of lack in fluidity and sometimes difficult to homogeneously mix with other ingredients because of their strong cohesiveness and their inferiority in compatibility.

In general those conventional fine silicone particles are prepared by an emulsion polymerization method. As a result, such particles have a spherical shape or a shape close thereto. While the spherical particles are used in a cosmetic material for the purpose of improving the sliding properties and reducing a tacky feel at the time the cosmetic material is applied to the skin, they lower the adhesiveness of the cosmetic material to the skin because of their shape. Therefore, it is usually tried to improve the adhesiveness by compounding an inorganic tabular powder, such as mica or sericite powder, into a cosmetic material.

However, those inorganic tabular powders have their specific gravity in the range of, 12–3, and so their specific gravity is greater than those of other ingredients to constitute a cosmetic material. In addition, they contain impurities because of natural materials, and so they are dull in color. Accordingly, when such heavy inorganic tabular powders are compounded into a liquid cosmetic material, they cause a problem of precipitation. Further, as the color of such powders become much darker when wetted by oil, compounding with them lowers the color saturation of the resultant cosmetic material.

SUMMARY OF THE INVENTION

The present invention is: made aiming chiefly at dissolving the aforementioned problems. More specifically, a first object of the invention is to provide an organic silicone powder which, when it is compounded with other ingredients into a composition, does not arise in users of the composition an uncomfortable feeling, such as a hard feel or a tacky touch, which is the problem of conventional resin powders of hydrocarbon or silicone type, and forms no sediment because of its low specific gravity, and further can improve the texture of the composition, including the gloss and the touch thereof, and the impressions that the users have upon application thereof, such as spreadability and feels.

A second object of the invention is to provide a method of producing the organic silicone resin powder as mentioned above.

A third object of the invention is to provide a cosmetic material comprising a powder which can impart improved moist or dry feel, and enhanced refreshing effect to the cosmetic material, can elevate not only application characteristics, including spreadability, but also adhesiveness, and further has improved specific gravity, compatibility and dispersibility to form no deposit.

One of the subject matters of the invention is an organic silicone resin powder that has a tabular shape the aspect ratio of which is greater than about 1 land comprises a copolymer produced by polymerization reaction between an organopolysiloxane containing at least one reactive group and at least one kind of monomer or oligomer capable of reacting to the reactive group. Therein, the reactive group may be a radical polymerizable group, while the monomer or oligomer may have radical polymerizability. This organic silicone resin powder may further comprise an inorganic powder.

Another subject matter of the invention is a method of producing an organic silicone resin powder having a tabular shape the aspect ratio of which is greater than about 1, with the method comprising the steps of forming a film from a copolymer produced by polymerization reaction between an organopolysiloxane containing at least one reactive group and at least one kind of monomer or oligomer capable of reacting to the reactive group, grinding the film into a powder, and then putting the powder through a sieve. Therein, the film may be formed using a biaxial extruder.

Still another subject matter of the invention is a cosmetic material which contains an organic silicone resin powder having a tabular shape the aspect ratio of which is greater about 1 and comprising: a copolymer produced by polymerization reaction between an organopolysiloxane containing at least one reactive group and at least one kind of monomer or oligomer capable of reacting to the reactive group. In such a cosmetic material, the foregoing organic silicone resin powder may be contained in a proportion of from about 0.01 to about 50 weight %. In addition, the number average molecular weight of the foregoing copolymers may be from about 2,000 to about 100,000. Further, the cosmetic material may further contain at least one ingredient selected from the group consisting of oils, surfactants and powders.

Herein, the term "aspect ratio" is defined as the b/a ratio, when the thickness of a resin powder particle is taken as "a" and the major axis thereof is taken as "b". Therefore, the particles are regarded as more tabular the greater their aspect ratio is.

DETAILED DESCRIPTION OF THE INVENTION

The preferred embodiments of the present invention are illustrated below. However, the invention should not be construed as being limited to these embodiments.

The particles constituting the present organic silicone resin powder have a tabular shape, and the thickness thereof is in the range of about 0.1 μm to about 2 μm. Considered from the standpoints of easiness of handling and impressions created by the application thereof, it is desirable that their average particle diameter on a volume equivalent basis ($D_p50$) be from about 0.1 to about 100 μm, particularly preferably from 1 to 50 μm. A reason therefor is in that when the thickness and diameter of particles are smaller than the foregoing range the gloss, which is characteristic of;powder, tends to be lost; while the particles having greater thickness and diameter than the foregoing range tend to give a rough feel.

Although the organic silicone resin powder having an aspect ratio greater than about 1 can serve the present purpose, it is desirable for the powder to have its aspect ratio in the range of 5 to 50 in order to further enhance its effects and make them more certain.

The reactive group-containing organopolysiloxanes and the monomers or oligomers capable of reacting to the reactive groups contained in such organopolysiloxanes, which are usable in producing copolymers according to the present invention, are illustrated below.

The reactive group-containing organopolysiloxanes usable in the invention are represented by the following formula;

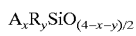

$$A_xR_ySiO_{(4-x-y)/2}$$

wherein A is a reactive group, R is a univalent hydrocarbon group containing 1 to 10 carbon atoms, x is from 0.002 to 1.5 and y is from 0 to 3.0, provided that $1.5 \leq x+y \leq 2.5$.

The R groups which constitute the foregoing organopolysiloxane molecule may be the same or different.

The reactive group represented by A is intended to include functional groups having chemical reactivity. Suitable examples of such a functional group include an amino group, a hydroxyl group, an epoxy group, a carboxylic acid group, and radical polymerizable groups, such as vinyl, styryl, α-methylstyryl, acryl and methacryl groups.

Specifically, the reactive group-containing organopolysiloxanes are, e.g., amino-modified silicones, alcohol-modified silicones, epoxy-modified silicones, carboxylic acid-modified silicones, vinyl-modified silicones, styrene-modified silicones, bisphenol A-modified silicones, acrylic-modified silicones, methacryl-modified silicones, or maleic anhydride-modified silicones.

Of the reactive group-modified silicones as recited above, the modified silicones having acrylic reactive groups, such as acrylate or methacrylate groups, are preferred over the others because of their high reactivity, easiness of reaction control and easy availability of raw materials.

As far as organopolysiloxanes have at least one reactive group in their respective organopolysiloxane skeletons, they can serve the present purpose. And, considering the reactivity, it is desirable for the reactive:group to be situated at a terminal position of organopolysiloxane molecule.

Also, the organopolysiloxanes containing two or more of reactive groups per molecule can be used in the invention, as seen from the definition of x and y in the formula illustrated above, and those reactive groups may be the same or different. In addition, the organopolysiloxane used in the invention may have not only a linear skeleton but also a branched skeleton.

Further, the organopolysiloxane used in the invention may be a mixture of two or more of reactive group-containing organopolysiloxanes differing in molecular weight.

As far as the reactive group-containing organopolysiloxane selected from the aforementioned range is employed, the resultant organic silicone resin powder can have improved spreadability and give desirable impressions, e.g., a moist feel, to users.

The reactive monomers or oligomers usable for the production of copolymers according to the present invention are monomers or oligomers which each have a functional group capable of reacting to the reactive groups contained in the organopolysiloxanes mentioned above. More specifically, when the reactive group contained in an organopolysiloxane used in copolymerization is an amino group, an alcoholic group, an epoxy group, a carboxylic acid group or a radical polymerizable group, the reactive group of the monomer or oligomer to be selected for the copolymerization is a functional group as a counterpart of the above-recited reactive group, namely an epoxy group, a carboxylic acid group, an amino group, an alcoholic group or a radical polymerizable group respectively.

In view of high reactivity, easy control of reaction and easy availability of raw materials, similarly to the case of the foregoing reactive group-containing organopolysiloxanes, it is desirable for the reactive monomer or oligomer to be a monomer containing a radical polymerizable group or an oligomer thereof. Suitable examples of such a monomer or oligomer include α-olefins (such as ethylene, propylene, butene, pentene, 4-methylpentene, hexene, heptene, octene, vinylcyclohoxene, styrene, a-methylstyrene, vinyltoluene, vinylethylbenzene, vinylxylene, p-t-butylstyrene and α-methyl-p-methylstyrene), acrylonlitrile, acrylic acid, methacrylic acid, methyl acrylate, methyl methacrylate, butyl acrylate, 2-hydroxyethyl acrylate, 2-hydroxypropyl acrylate, 2-ethylhexyl acrylate, isobornyl acrylate, dicyclopentenyl acrylate, 2-hydroxyethyl methacrylate, N,N- diemthylacrylamide, N-vinylacetamde, N-vinylpyrrolidone, N-vinylcaprolactam, acryloylmorpholine, N-vinylimidazole, maleic anhydride, phenylimide, and oligomers of the monomers as recited above.

Also, the reactive monomer may be a polyfunctional monomer, such as tricyclodecanedimethanol diacrylate, pentaerythritol triacrylate, trimethylolpropane triacrylate or polyethylene (propylene) glycol diacrylate.

The reactive group-containing organopolysiloxane and the reactive monomer or oligomer a re properly selected from their respective exemplifications as recited above, and subjected to copolymerization reaction. In a special case where organopolysiloxanes are grafted onto an organic resin by copolymerization of a radical polymerizable monomer and a radical polymerizable group-containing organopolysiloxane, it is advantageous to use an organopolysiloxane having a radical polymerizable group at one end of the siloxane chain.

The foregoing radical polymerizable monomer and radical polymerizable group-containing organopolysiloxane can be copolymerized in a conventional manner using a radical initiator, such as benzoyl peroxide or azobisisobutyronitrile. As to the method for copolymerization, any method of emulsion polymerization, solution polymerization and block polymerization may be adopted therein.

When the thus produced copolymer has hydroxyl groups, it may be further reacted with a dibasic acid anhydride to convert a part of the hydroxyl groups into carboxyl groups, thereby producing a modified copolymer.

Further, the modified copolymer thus produced can be neutralized with an alkali solution to be further converted into the carboxylic acid salt.

The copolymers produced using the aforementioned methods have their individual weight average molecular weight in the range of 2,000 to 100,000, preferably 5,000 to 60,000.

When the copolymer has a weight average molecular weight lower than 2,000, the powder thereof is brittle, and the cosmetic material mixed therewith tends to have a tacky feel. When the copolymer has a weight average molecular weight higher than 100,000, on the other hand, the powder thereof is apt to have high hardness, and so the; cosmetic material mixed therewith tend to have a rough feel. Therefore, it is desirable for the present copolymers to have their individual molecular weight within the foregoing limits. Additionally, the aforementioned drawbacks are certain to be removed as far as the weight average molecular weight is from 5,000 to 60,000.

Further, it is desirable that the compounding ratio of reactive group-containing organopolysiloxanes to reactive monomers or oligomers be in the range of 0.1/99.9 to 50/50, particularly from 5/95 to 30/70, by weight.

When the reactive group-containing organopolysiloxane is compounded in a proportion lower than 0.1 weight %, the resultant copolymer sometimes rails to exhibit marked characteristics of organopolysiloxanes, including slipping properties; while, when it is compounded in a proportion higher than 50 weight %, the glass transition temperature thereof is liable to drop, the composition containing the resultant copolymer, such as a cosmetic material, tends to arise an uncomfortable feeling, e.g., a stiff feel, in users.

Then, if the foregoing compounding ratio is selected from the range of 5/95 to 30/70 by weight, it becomes certain that the resultant copolymer can exhibit marked characteristics of organopolysiloxanes, such as slipping properties, and can have a glass transition temperature of at least 40° C. to arise no uncomfortable feeling.

For raising the molecular weight of the present copolymers, various methods can be adopted, with examples including a method of controlling the compounding ratio upon copolymerization, a method of carrying out copolymerization using at least two kinds of compounds for either or both of copolymerizable monomers (namely a reactive monomer or oligomer and a reactive group-containing organopolysiloxane), a method of carrying out copolymerization using a polyfunctional group-introduced compound for either of copolymerizable monomers, and a method of carrying out the copolymerization of a reactive monomer or oligomer and a reactive group-containing organopolysiloxane in the presence of compounds reactive to the monomer or the oligomer and/or the organopolysiloxane.

More specifically, when an olefin monomer containing a carboxylic acid group is chosen as the reactive monomer, the olefin monomer can undergo not only the dehydration condensation reaction with an organopolysiloxane having alcoholic group(s) reactive to the carboxylic acid group and a polyhydric alcohol, such as glycol, but also radical polymerization, thereby producing a copolymer.

In another case of copolymerization, the olefin monomer containing an epoxy group instead of the carboxylic acid group in the foregoing case is chosen as the reactive monomer, and the addition reaction may be carried out using such an olefin monomer in combination with an organopolysiloxane containing amino group(s) instead of the alcoholic group(s) in the foregoing case and an amino compound.

Instead of using polyfunctional reactive monomers in the copolymerization reaction, the organopolysiloxane used therein maybe chosen from polyfunctional organopolysiloxanes.

In the next place, the method of preparing the present organic silicone resin powder having a tabular shape and an aspect ratio greater than about 1, which can be mixed in cosmetic materials, is illustrated below.

After the copolymer is produced in accordance with any of the aforementioned methods, the resin component is separated by distilling off the solvent, or it is reprecipitated as a powdery matter with methanol or the like and then filtered off.

During, before or after the copolymerization reaction, an inorganic matrix, such as an inorganic powder (e.g., titanium oxide, mica or titanium mica), a pearl brightener or an inorganic pigment, and general additives for synthetic resins, such as a lubricant (e.g., silicone oil), an antistatic agent, an ultraviolet absorbent and an antioxidant, can be added to the reaction system.

Thus, the powder having the desired outward appearance, which was impossible for conventional inorganic powders to have, can be obtained.

The resin component thus obtained is made into a tabular powder in a manner as described below: For instance, the resin component is dissolved in an organic solvent, made into a thin film, and then ground into a powder. In another manner, the resin component may be formed into a film by means of a biaxial extruder, and further stretched. In still another manner, the powder obtained by reprecipitation may be dried, and then ground into a fine powder. Anyhow, a tabular powder which can make the same impression as mica on users can be formed by coating a solution of resin component on a base in a filmy layer, similarly to the case of preparing release paper, peeling the layer away from the base and then grinding it.

In pulverizing the resin component obtained, hitherto known grinder, such as a primary crusher (e.g., a cutter mill, a hammer mill or a jaw crusher) or a pulverizer (e.g., a stamp mill, a jet mill, a ball mill, a roller mill, a pin-type mill or an impeller mill), may be employed. Additionally, the apparatus as recited above may be used under a cooled or heated condition.

The thus obtained powder is sifted out by means of a classifier to prepare organic silicone resin particles having a tabular shape and the desired diameter and aspect ratio.

Further, the tabular particles thus prepared may undergo a surface treatment using, e.g., metal soap, alumina, silica or phosphoric acid.

The average particle diameter of tabular powder on a volume equivalent basis ($D_p50$) is determined by a screening method, a laser method or a centrifugal sedimentation method. The average thickness of tabular particles is calculated by selecting several particles arbitrarily from the particles in the visual field of an electron microscope, measuring their respective thicknesses, and calculating the average value of the measured values. And the aspect ratio is calculated from the thus measured average particle diameter and thickness.

The organic silicone resin powder prepared in the manner as mentioned above is mixed as one ingredient of a cosmetic material in a proportion of, e.g., 0.01 to 50 weight %.

When the proportion of the powder mixed is smaller than 0.01 weight %, the resultant cosmetic material cannot have desirable feels, such as a dry feel, in some cases; while the proportion increased beyond 50 weight % tends to impair the applicability of the resultant cosmetic material, such as smooth and even spreadability. Therefore, it is desirable for the proportion of the powder mixed to be in the foregoing range. The more suitable range thereof is from 0.05 to 20 weight %, and this range is certain to remove the foregoing drawbacks.

The cosmetic materials containing the aforementioned organic silicone resin powder can have a remarkable reduction in specific gravity, compared with those containing conventional inorganic powders, so that they can successfully avoid precipitating the powder by aging.

Further, even an uncomfortable texture, such as a rough or tacky touch, the cosmetic materials tend to have when they contain a conventional resin of hydrocarbon type or silicone type respectively as an ingredient thereof, can be dissolved by adding thereto the present organic silicone resin powder which is made up of a copolymer having improved compatibility and dispersibility, and further has a tabular shape having an aspect ratio greater about 1. Moreover, the addition of the present organic silicone resin powder makes it possible to impart only the advantageous properties each resin has by nature, such as stability and a moist feel, to cosmetic materials.

As mentioned above, the present powder is remarkably improved in not only properties but also easiness of handling, compared with hitherto employed inorganic powders, so that it can be a highly satisfactory substitute for conventional inorganic powders.

In the cosmetic materials according to the invention, other ingredients can be mixed, with examples including the following:

A wide variety of oils can be mixed depending on the intended purpose of the cosmetic material to be prepared. The oils mixed may be in any of solid, semisolid and liquid states.

More specifically, not only natural animal and vegetable fats and oils but also semi-synthetic fats and oils are usable in the present cosmetic material. Examples thereof include avocado oil, linseed oil, almond oil, insect wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chaisese tung oil, cinnamon oil, jojoba wax, shellac wax, turtle oil, soybean oil, tea seed oil and tsubaki oil.

Other Examples of natural animal and vegetable fats and oils and semi-synthetic fats and oils which can be used herein include evening primrose oil, corn oil, lard, rape seed oil, Japanese tung oil, rice-bran wax, germ oil, horse fat, persic oil, palm oil, palm kernel oil, castor oil, hydrogenated castor oil, methyl caster oil fatty acid, sunflower oil, grape seed oil, bayberry wax, jojoba oil, macadamia nut oil, beeds wax, mink oil, cottonseed oil, cotton.:wax, Japan wax, haze kernel oil, montan wax, coconut oil, hydrogenated coconut oil, tricoconut oil fatty acid glyceride, mutton-tallow, peanut oil, anhydrous lanolin, hard lanolin, lanolin acetate, lanolin fatty acid isopropyl, hexyl laurate, POE lanolin alcohol ether, POE lanolin alcohol acetate, polyethylene glycol lanolin fatty acid, POE hydrogenated lanolin alcohol ether, and egg yolk oil.

As examples of hydrocarbon oil which can be added, mention may be made of ozokerite, squalane, squalene, ceresine, paraffin, liquid paraffin, pristane, polyisobutylene, microcrystalline wax and Vaseline.

As examples of a higher fatty acid which can be added, mention may be made of lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

As examples of a higher, alcohol which can be added, mention may be made of lauryl alcohol, myristyl alcohol, stearyl alcohol, behenyl alcohol, hexadecyl alcohol, oleyl alcohol, isostearyl alcohol, hexyldecanol, octyldodecanol, cetostearyl alcohol, 2-decyltetradecinol, cholesterol, phytosterol, POE cholesterol ester, glycerin monostearyl (batyl alcohol) and monooleyl glycerin ether (cerakyl alcohol).

As examples of ester oil which can be added, mention may be made of dilsobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethyilhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate and butyl stearate.

Other examples of usable. esters include diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, 2-octyldodecyl myristate, 2-hexyldecyl myristate, myristyl myristate,hexyldecyl dimethylocanoate, ethyl laurate, hexyl laurate,: N-lauroyl-L-glutaminic acid 2-octyldodecyl ester and diisostearyl malic acid.

As examples of glyceride oil which can be added, mention may be made of acetoglyceride, triisooctanoic acid glyceride, triisostearic acid glyceride, triisopalmitic acid glyceride, tri-2-ethylhexanoic acid glyceride, monostearic acid glyceride, di-2-heptylundecanoic acid glyceride and trimyristic acid glyceride.

As examples of silicone oil which can be added, mention may be made of dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetirasiloxane, higher alkoxy-modified silicones such as stearoxysilicone, and higher fatty acid-modified silicones.

As examples of fluorine-containing oil which can be added, mention may be made of perfluoropolyether, perfluorodecalin and perfluorooctane.

Additionally, the oils recited above may be added alone or as mixtures of at least two among them.

Further, the present cosmetic material can contain a surfactant, if desired, and has no particular restriction as to the type of surfactant used. In other words, any of anionic, cationic, amphoteric and nonionic surfactants can be used therein.

Examples of a usable anionic surfactant include fatty acid soap, such as sodium stearate and triethanolamine palmitate; polyoxyethylene fatty alcohol ether carboxylic acids and salts thereof; carboxylates, such as condensates of amino acids and fatty acids; alkylsulfonate; alkenesulfonate; sulfonated fatty acid ester; sulfonated fatty acid amide; alkylsulfonic acid-formaldehyde condensate; alkylsulfate; higher secondary alcohol sulfate; alkyl and aryl ether sulfate; fatty acid ether sulfate, fatty ;acid alkylolamide sulfate; ether sulfate, such as Turkeky red oil; alkyl phosphate; ether phosphate; alkyl aryl ether phosphate; amide phosphate; and active agents of N-acylamino acid type.

Examples of a usable cationic surfactant include amine salts, such as alkylamie salts, polyamines and aminoalcohol fatty acid derivatives, quaternary alkylammonium salts, quaternary arylammonium salts, pyridinium salts and imidazolium salts.

Examples of a usable amphoteric surfactant include betaine, aminocarboxylate and imndazoline derivatives.

Examples of a usable amphoteric surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hardened castor oil, polyoxyethylene phytostanol ehter, polyoxyethylene phytosterol ether, polyoxyethylene cholestanol ether, polyoxyethylene cholesteryl ether, polyoxyalkylene-modified organopolysiloxanes, organopolysiloxanes modified with both polyoxyalkylene and alkyl groups, alkanolamides, sugar ethers and sugar amides.

Furthermore, the following powders can be used in the present cosmetic material.

Such powders are not particularly restricted as to their shape, size and structure, and may have any shape, size and structure as far as the powders used in conventional cosmetic materials have them. Specifically, they may have any of spherical, acicular and tabular shapes, any of haze-particle, fine-particle and pigment-grade sizes and any of structures (e.g., a porous or nonporous structure).

When such a powder is mixed in the present cosmetic material, it is not limited to only one among the powders recited below, but may be used together with another powder equivalent in effect. In addition, the powders recited below may be used as a mixture of two or more thereof. The suitable amount of powders mixed is determined depending on the desired purpose.

Examples of an organic powder include polyamide powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, nylon powder, 12-nylon powder, 6-nylon powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder, polycarbonate resin powder, microcrystalline fiber powder, rice starch powder and lauroyl lysine.

Examples of a metal salt surfactant powder (metal soap powder) include zinc stearate, aluminum stearate, calcium stearate, magnesium stearate, zinc myristate, magensium myristate, zinc cetylphosphate, calcium cetylphosphate and zinc sodium cetylphosphate.

Examples of an inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, synthetic mica, muscovite, phlogopite, ruby mica, biotite, lipidolite, silidic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxie, boronnitride, silica, titanium mica, ironoxide red, iron oxide black, iron oxide yellow and barium ferrite. The inorganic powder as recited above may be added in advance to the present organic silicone resin powder, and then mixed in a cosmetic material.

The colors include both inorganic and organic pigments. The inorganic powders as recited above are comprised in the inorganic pigment. More specifically, the inorganic pigment includes inorganic red pigments, such as iron oxide iron hydroxide and iron titanate; inolrganic brown pigments, such as γ-iron oxide; inorganic yellowipigments, such as iron oxide yellow and loess; inorganic black pigments, such as iron oxide black and carbon black; inorganic violet pigments, such as Mango violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural pigments; and synthetic resin powder complexes of the inorganic pigments as recited above.

As examples of a pearl pigment, mention may be made of titanium oxide-coated mica, bismuth oxychloride, titanium oxide-coated bismuth oxychloride, titanium oxide-coated talc, fish scales, and titanium oxide-coated colored mica.

As examples of a metallic powder pigment, mention may be made of aluminum powder, copper powder and stainless powder.

The foregoing tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No.

203, Orange No. 204, Orange No. 206 and Orange No. 207 (according to the pigment nomenclature method in JIS).

The foregoing natural pigments include carminic acid, laccaic acid, carthamin, bradilin and crocin.

Additionally, complexes of the powders as recited above or those obtained by treating the aforementioned powders with general oil, silicone oil or fluorine-containing compound may be used. Of course, the powders as recited above may be used as a mixture of two or more thereof.

To the present cosmetic material, the ingredients used in general cosmetic materials, such as water, alcohols, water-soluble polymers, film-forming agents, oil-soluble gelling agents, clay minerals modified with organic compounds, resin, ultraviolet absorbents, moisture-holding agents, antiseptics, antibacterial agents, perfume, salts, antioxidants, pH regulators, chelating agents, tonic, skin beautifying components, vitamins, amino acids, nucleic acids, hormones and clathrate compounds, can be added so far as they have no adverse influence on the effects of the present invention.

Examples of usable alcohols include lower alcohols, such as ethanol and isopropanol; sugar alcohols, such as sorbitol and maltose; and sterols, such as cholesterol, phytosterol and lanosterol.

Examples of usable water-soluble polymers include vegetable polymers, such as gum arabic, tragacanth, arabine galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; and cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, microcrystalline cellulose and powdery cellulose.

As other examples of usable water-soluble polymers, mention may be made of alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium salts of polyacrylic acid, polyethylacrylate and polyacrylamide; polyethyleneimines; cationic polymers; and inorganic water-soluble polymers, such as bentonite, aluminum magnesium silicate, laponite, helctorite and silicic acid anhydride.

Therein, film-forming agents, such as polyvinyl alcohol and polyvinyl pyrrolidine, may be included.

Examples of an oil-soluble gelling agent which can be used herein include metal soaps, such as aluminum stearate, magnesium stearate and zinc myristate; amino acid derivatives, such as N-lauroyl-L-glutamic acid and α,γ-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of an ultraviolet absorbent which can be used herein include those of benzoic acid type, uch as p-aminobenzoic acid; hose of anthranilic acid type, uch as methyl anthrarilate; hose of salicylic ;acid type,such as methyl salicylate; those of succinic acid type, such as octyl p-methoxysuccinate; those of benzophenone type, such as 2,4-dihydroxybenzophenone; and those of urocanic acid type, such as ethyl urocanate.

Examples of a moisture-holding agent which can be used herein include sorbitol, xylitol, polyethylene glycol, hyaluromic acid, chondroitin sulfuric acid and pyrrolidone carboxylic acid.

Examples of an antiseptic which can be used herein include alkyl p-hydroxybenzoates, benzoic acid, sodium benzoate, sorbic acid, potassium siorbate and phenoxyethanol.

Examples of an antimacrobiall agent which can be used herein include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide,i photosensitizer and phenoxyethanol.

Examples of an antioxidant which can be used herein include tocopherol, butylhydroxyanisole, dibutylhydroxytoluene and γ-oryzanol.

Examples of a pH regulator which can be used herein include lactic acid, citric acid, glycolic acid, succinic acid, tartaric acid, dl-malic acid, potassium carbonate, sodium hydrogen carbonate and ammonium hydrogen carbonate.

Examples of a chelating agent which can be used herein include alanine, sodium ethylenediaminetetraacetate, sodium polyphosphate, sodium metaphosphate and phosphoric acid. Examples of a tonic which can be used herein include L-menthol and camphor.

Examples of an anti-inflammatory agent which can be used herein include allantoin, glycyrrhetinic acid, tranexamic acid and azulene.

Examples of a skin-beautifying component which can be used herein include whitening agents, such as placenta extract, arbutin, glutathione and Ykinoshita extract; cell activators, such as royal jelly, photosensitizer, cholesterol derivatives and calf blood extract; and rough dry skin improvers, including blood circulation improvers such asnonylic acid vanillyl amide, benzyl nicotinate, β-butoxyethyl nicotinate, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol, skin astringents such as zinc oxide and tannic acid, and anti-seborrheic agents such as sulfur and thianthol.

Examples of vitamins which can be used herein include vitamin A, such as vitamin A oil, retinol, retinyl acetate and retinyl palmitate; vitamin $B_2$, such; as riboflavin, riboflavin buyrate and flavin adenine nucleotide; vitamin $B_6$, such as pyridoxine hydrochloride and pyridoxine dioctanoate; vitamin C, such as L-ascorbic acid, L-ascorbic acid dipalmitic ester, disodium (L-ascorbic acid)-2-sulfate and dipotassium dl-α-tocopherol-L-ascorbic acid phosphoric diester; vitamin D, pantothenicacids, such as calciumpiantothenate, D-pantothenyl alcohol, pantothenyl ethyl ether and acetylpantothenyl ethyl ether, ergocalciferol and cholecarciferol; vitamin E, including nicotinic acids such as nicotinic acid, benzyl nicotinate and nicotinic acid amide, dl-α-tocopherol, dl-α-tocopheryl acetate, dl-α-tocopheryl nicotinate and dl-α-tocopheryl succinate; vitamin P; and biotin.

Examples of an amino acid which can be used herein include alginine, aspartic acid, cystine, cysteine, methionine, serine, leucine and tryptopphan; an example of usable nucleic acids is deoxyribonucleic aicd; and examples of usable hormone are estradiol and ethenyl estradiol.

The term "cosmetic material" as used herein are intended to include preparation products in all fields where the feel is regarded as important when they are put on the skin, including not only cosmetics but also medicines for external application, and further enamel for manicure and hairdressing products.

More specifically, the present cosmetic material includes skin care products, such as face lotion, milky lotion, cream, facial pack, massage articles, lip cream, hand cream and cleaning articles; makeup products, such as face powder, foundation, rouge, eye shadow, mascara, eyeliner, eyebrow articles, overcoat articles and lipstick; nail-beautifying articles, such as enamel for manicure; and hairdressing products, such as shampoo, rinse, rinse-in-shampoo, treatment, conditioner, hair cream, hair oil, brushing articles, hair-set articles and hair tonic.

Additionally, the present cosmetic material may have any of forms, including liquid, emulsion, solid, cream, paste, multi-layer, mousse, gel and spray forms, if desired.

Besides the cosmetics, the present organic silicone resin powder can be used in the field of coating, e.g., for a releasable coating agent, a protective coating agent, a water-repellant coating agent, printing ink, coating color or wax.

The present invention will now be illustrated in greater detail by reference to the following examples and comparative examples.

Additionally, the entire disclosure of all applications, patents and publications, cited .above and below, and of corresponding Japanese applications No. 11-038039 and 11-039532, filed on February 17 and February 18 respectively in 1998, is hereby incorporated by reference.

EXAMPLE 1

Preparation of Tabular Powder of Organic Silicone Resin

Toluene in an amount of 100 parts was placed in a glass-made reaction vessel equipped with a stirrer, a reflux condenser, a thermometer and a nitrogen introduction tube, and thereinto nitrogen gas was blown to remove the dissolved oxygen from the toluene. Thereto, 70 parts by weight of styrene and 30 parts by weight of Organopolysiloxane (1) represented by the following formula (i) were added, and then 0.2 parts by weight of azobisisobutyronitrile was added as the reaction vessel was kept at a temperature of 80° C.

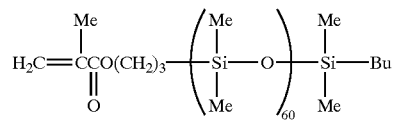

(i)

Further, 0.2 parts by; weight portions of azobisisobutyronitrile were added at intervals of two hours till the non-volatile component concentration in the reaction solution was increased beyond 50%. After the reaction was completed, the resulting solution was cooled to room temperature, and poured into 300 parts by weight of methanol to deposit a colorless powdery resin. The thus deposited resin was filtered off, dried, and examined for molecular weight and glass transition point by GPC measurement and differential scanning calorimetry (DSC), respectively. Thus, it was found that the weight average molecular weight of the resin obtained was 43,000 on a polystyrene basis and the glass transition point thereof was 62° C.

The thus synthesized resin was dissolved in toluene, applied to an aluminum plate, and then dried to form a film. The film thus formed was ground into a powder by a jet mill, and put through a 325-mesh sieve. Thus, a tabular powder of organic silicone resin having an average particle size of 30 μm was obtained. The particles constituting the thus obtained tabular powder had an average aspect ratio of 32, determined from electron micrographs thereof.

EXAMPLE 2

Preparation of Tabular Powder of Organic Silicone Resin

Toluene in an amount of 40 parts was placed in a glass-made reaction vessel equipped with a stirrer, a reflux condenser, a thermometer and a nitrogen introduction tube, and thereinto nitrogen gas was blown to remove the dissolved oxygen from the toluene. Thereto was added dropwise a mixture of 24 parts by weight of methyl methacrylate, 6 parts by weight of butyl methacrylate, 4 parts by weight of 2-hydroxyethyl acrylate and 6 parts by weight of Organopolysiloxane (2) represented by the following formula together with 0.6 parts by weight of azobisisobutyronitrile while keeping the reaction vessel temperature at 90° C.

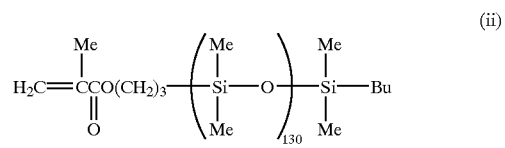

(ii)

After 2-hour lapse, the reaction solution was further mixed with 0. 2 parts by weight of azobisisobutyronitrile, and ripened for five hours to complete the reaction. After the completion of the reaction, the resultant solution was cooled to room temperature, and thereto methyl ethyl ketone was added to thoroughly dissolve the resin component, followed by filtration.

The thus obtained synthetic resin solution was processed in the same manner as in Example 1, thereby preparing a tabular powder of organic silicone resin having a weight average molecular weight of 28, 000 and a glass transition point of 80° C. And the organic silicone resin powder obtained herein had an powder of organic silicone resin having a weight average molecular weight of 28,000 and a glass transition point of 80° C. And the organic silicone resin powder obtained herein had an average particle size of 24 μm and an average aspect ratio of 28.

EXAMPLE 3

Preparation of Tabular Powder of Organic Silicone Resin

The foregoing Organopolysiloxane (2) in an amount of 10 parts by weight and methyl ethyl ketone in an amount of 60 parts were placed in a glass-made reaction vessel equipped with a stirrer, a reflux condenser, a thermometer and a nitrogen introduction tube, and thereinto nitrogen gas was blown to remove the dissolved oxygen. Thereto were added dropwise a mixture of 26 parts by weight of methyl methacrylate with 4 parts by weight of methacrylic acid and 0.2 parts by weight of azobisisobutyronitrile while keeping the reaction vessel temperature at 80° C. After 7-hour lapse, 0.2 parts by weight of azobisisobutyronitrile was further added to the reaction solution, and the ripening was carried out for four hours to complete the reaction. After the completion of the reaction, the resultant solution was cooled to room temperature, and poured into 300 parts by weight of methanol to precipitate a colorless powdery resin.

The powdery resin obtained was dissolved in methyl ethyl ketone, and the resultant resin solution was processed in the same manner as in Example 1, thereby preparing a tabular powder of organic silicone resin having a weight average molecular weight of 32,000 and a glass transition point of 110° C. And the organic silicone resin powder obtained herein had an average particle size of 15 μm and an average aspect ratio of 19.

EXAMPLE 4

Preparation of Tabular Powder of Organic Silicone Resin

Toluene in an amount of 100 parts was placed in a glass-made reaction vessel equipped with a stirrer, a reflux condenser, a thermometer and a nitrogen introduction tube, and thereinto nitrogen gas was blown to remove the dissolved oxygen from the toluene. Thereto, 70 parts by weight of styrene, 30 parts by weight of Organopolysiloxane (1) illustrated above and 0.5 parts by weight of tri-methoxymethacryloylpropylsilane were added, and then 0.2 parts by weight of azobisisobutyronitrile was added as the reaction vessel was kept at a temperature of 80° C. Further, 0.2 parts by weight portions of azobisisobutyronitrile were added at intervals of two hours till the non-volatile component concentration in the reaction solution was increased beyond 50%. After the reaction was completed, a small portion of the reaction solution was taken out, dried, and subjected to molecular weight measurement by GPC. The thus determined weight average molecular weight of the reaction product was 45,000 on a polystyrene basis. Then, the reaction solution was mixed with 2 parts by weight of fine grain titanium oxide, and the stirring thereof was further continued under heating. The thus treated reaction solution was cooled to room temperature, and poured into 300 parts by weight of methanol to deposit a colorless powdery resin. The thus deposited resin was examined for glass transition point by DSC. And the glass transition point thereof was found to be 64° C.

The thus synthesized resin was dissolved in toluene, applied to an aluminum plate, and then dried to form a film. The film thus formed was ground into a powder by a jet mill, and put through a 325-mesh sieve. Thus, a tabular powder of organic silicone resin having an average particle size of 28 μm was obtained. The particles constituting the thus obtained tabular powder had an average aspect ratio of 25, determined from electron micrographs thereof.

EXAMPLE 5

The tabular powder of organic silicone resin prepared in Example 1 was mixed with the following ingredients, and made into milky lotion in the process described below:

| Ingredients | Amount mixed (%) |
| --- | --- |
| 1. Microcrystalline wax | 1.0 |
| 2. Lanolin | 1.0 |
| 3. Dimethylpolysiloxane (6 cs) | 40.0 |
| 4. Dimethylpolysiloxane (>1,000,000 cs) | 2.0 |
| 5. Tabular powder of organic silicone resin | 2.0 |
| 6. Sorbitan sesquioleic acid ester | 4.0 |
| 7. Polyoxyethylene (20) sorbitan monooleic acid ester | 1.0 |
| 8. 1,3-Butylene glycol | 5.0 |
| 9. Antiseptic | proper |

-continued

| Ingredients | Amount mixed (%) |
| --- | --- |
| 10. Perfume | proper |
| 11. Purified water | the rest |

[Making Process]
A: The ingredients 1 to 7 were mixed together under heating to prepare a mixture A.
B: The ingredients 8, 9 and 11 were mixed together, added to the mixture A, and made into an emulsion B.
C: The emulsion B was cooled, and thereto the ingredient 10 was added.

The thus prepared milky lotion had no tackiness and went on quite well when applied to the skin, caused dry and refreshed feels in the applied skin, and had a very smooth texture.

EXAMPLE 6

The tabular powder of organic silicone resin prepared in Example 2 was mixed with the following ingredients, and made into a skin cleaning agent in the process described below:

| Ingredients | Amount mixed (%) |
| --- | --- |
| 1. Myristic acid | 15.0 |
| 2. Palmitic acid | 5.0 |
| 3. Stearic acid | 3.0 |
| 4. Beeds wax | 3.0 |
| 5. Polyethylene glycol 6000 | 2.0 |
| 6. Ethylene glycol distearate | 2.0 |
| 7. Coconut oil fatty acid diethanolamide | 3.0 |
| 8. Glycerin | 15.0 |
| 9. Antiseptic | proper |
| 10. Potassium hydroxide | 5.5 |
| 11. Purified water | the rest |
| 12. Sodium N-lauroylsarcosine | 10.0 |
| 13. Tabular powder of organic silicone resin (aspect ratio: 28) | 2.0 |

[Making Process]
A: The ingredients 1 to 9 were mixed together under heating to prepare a mixture A.
B: The ingredients 10 and 11 were mixed together under heating to prepare a mixture B.
C: The mixture B was added to the mixture A to prepare a homogeneous solution. To this solution, the ingredients 12 and 13 were further added, and made into a homogeneous matter. This matter was cooled with stirring to prepare a skin cleaning lotion.

The thus prepared skin cleaning lotion went on quite well and produced massage effect when applied to the skin, and brought about dry and refreshed feelings without attended by a stiff feeling after it was washed away.

EXAMPLE 7

The tabular powder of organic silicone resin prepared in Example 3 was mixed with the following ingredients, and made into compressed face powder (such as the so-called Pan-Cake) in the process described below:

| Ingredients | Amount mixed (%) |
| --- | --- |
| 1. Titanium oxide | 5.0 |
| 2. Kaolin | 5.0 |
| 3. Talc | the rest |
| 4. Zinc myristate | 5.0 |

| Ingredients | Amount mixed (%) |
|---|---|
| 5. Iron oxide red | 0.7 |
| 6. Iron oxide yellow | 2.1 |
| 7. Iron oxide black | 0.2 |
| 8. Tabular powder of organic silicone resin (aspect ratio: 19) | 15.0 |
| 9. Porous globular silica | 10.0 |
| 10. Squalane | 3.0 |
| 11. Glyceryl trioctanoate | 2.0 |
| 12. Antiseptic | proper |
| 13. Perfume | proper |

[Making Process]
A: The ingredients 1 to 9 were mixed together to prepare a mixture A.
B: The ingredients 10 to 12 were mixed together, and then added to the mixture A to prepare a mixture B.
C: The ingredient 13 was added to the mixture B and mixed therein homogeneously. The resultant matter was compressed tightly into a metal pan, thereby obtaining face powder according to the invention.

The face powder thus compressed had a dry and smooth texture, spread smoothly, and stayed well due to its good adhesiveness. Thus, the present face powder can produce a beautiful makeup result and the result wears well.

EXAMPLE 8

The tabular powder of organic silicone resin prepared in Example 2 was mixed with the following ingredients, and made into face powder in the process described below:

| | Ingredients | Amount mixed (%) |
|---|---|---|
| 1. | Titanium oxide | 12.0 |
| 2. | Zinc oxide | 10.0 |
| 3. | Kaolin | 10.0 |
| 4. | Talc | the rest |
| 5. | Iron oxide red | 0.8 |
| 6. | Iron oxide yellow | 2.5 |
| 7. | Iron oxide black | 0.2 |
| 8. | Tabular powder of organic silicone resin (aspect ratio: 28) | 18.0 |
| 9. | Cured silicone rubber powder (*1) | 5.0 |
| 10. | Liquid parrafin | 4.0 |
| 11. | Octamethylcyclotetrasiloxane | 5.0 |
| 12. | Dimethylpolysiloxane | 5.0 |
| 13. | Isopropyl palmitate | 3.0 |
| 14. | Glycerin | 3.0 |
| 15. | Antiseptic | proper |
| 16. | Perfume | proper |

*1: KSP-100 (globular particles having an average size of 5 μm, produced by Shin-Etsu Chemical Co., Ltd.)
[Making Process]
A: The ingredients 1 to 9 were mixed together to prepare a homogeneous mixture A.
B: The ingredients 10 to 15 were mixed together, and then added to the mixture A to obtain a mixture B.
C: The ingredient 16 was added to the mixture B, and the resultant matter was compressed tightly into a metal pan.

The thus prepared face powder according to the invention had a quite dry and smooth texture, spread smoothly, and stayed well due to its good adhesiveness. Thus, the present face powder can produce a beautiful makeup, result, and the result wears well.

EXAMPLE 9

The tabular powder of organic silicone resin prepared in Example 3 was mixed with the following ingredients, and made into foundation in the process described below:

| Ingredients | Amount mixed (%) |
|---|---|
| 1. Silicone-treated titanium oxide | 7.0 |
| 2. Tabular powder of organic silicone resin (aspect ratio: 19) | 6.0 |
| 3. Silicone-treated iron oxide red | 0.5 |
| 4. Silicone-treated iron oxide yellow | 1.3 |
| 5. silicone-treated iron oxide black | 0.2 |
| 6. Liquid parrafin | 5.0 |
| 7. Dimethylpolysiloxane | 8.0 |
| 8. Octamethylcyclotetrasiloxane | 12.0 |
| 9. Perfluoropolyether | 2.0 |
| 10. Octyl paramethoxysuccinate | 2.0 |
| 11. Dextrin palmitic acid ester | 2.0 |
| 12. Sorbitan sesquioleic acid ester | 1.5 |
| 13. Polyether-modified silicone (*2) | 3.0 |
| 14. 1,3-Butylene glycol | 1.5 |
| 15. Glycerin | 7.0 |
| 16. Antiseptic | proper |
| 17. Perfume | proper |
| 18. Purified water | the rest |

*2: KF-6017 (produced by Shin-Etsu Chemical Co. Ltd.)
[Making Process]
A: The ingredients 6 to 13 were mixed together under heating. Thereto, the ingredients 1 to 5 were added and mixed homogeneously to prepare a mixture A.
B: The ingredients 14, 15, 16 and 18 were mixed together under heating to obtain a mixture B.
C: The mixture B was added to the mixture A, and made into an emulsion. The emulsion was cooled, and then the ingredient 17 was added thereto.

The thus prepared foundation according to the invention was fluent and smooth, spread smoothly, and stayed well due to its good adhesiveness. Thus, the present foundation can produce a beautiful makeup result, and its effect lasts well.

EXAMPLE 10

The tabular powder of organic silicone resin prepared in Example 4 was mixed with the following ingredients, and made into eye shadow sticks in the process described below:

| Ingredients | Amount mixed (%) |
|---|---|
| 1. Gypsum | 35.0 |
| 2. Talc | 17.5 |
| 3. Pigment | 10.0 |
| 4. Nylon powder | 15.0 |
| 5. Tabular powder of organic silicone resin (aspect ratio: 25) | 15.0 |
| 6. Squalane | 3.0 |
| 7. Polyoxyethylene sorbitan monooleic acid ester | 0.5 |
| 8. Glycerin | 4.0 |
| 9. Antiseptic | proper |
| 10. Perfume | proper |
| 11. Purified water | (100) |
| 12. Ethanol | (50) |

[Making Process]
A: The ingredients 1 to 5 were mixed together to prepare a mixture A.
B: The ingredients 6 to 12 were mixed together to prepare a mixture B.
C: The mixture A was added to the mixture B, and the resultant mixture was charged in a container, allowed to stand for hardening, and then dried.

Additionally, the ingredients 11 and,12 were used for hardening the ingredient 1 (gypsum) but they vaporized during the drying treatment; as a result, the mixture obtained were free of them. Therefore, the amounts, of these ingredients used are given above in parentheses.

The thus obtained eye shadow, sticks according to the invention had a good appearance and a dry and smooth texture, spread lightly and smoothly, stayed well due to their good adhesiveness. Thus, the present eye shadow stick can produce a beautiful makeup result, and the result wears well. In addition, the present eye shadow stick gave no powdery impression and was easily shaded off when put on eyelid.

EXAMPLE 11

The tabular powder of organic silicone resin prepared in Example 3 was mixed with the following ingredients, and made into lipstick in the process described below:

| Ingredients | Amount mixed (%) |
| --- | --- |
| 1. Paraffin wax | 12.0 |
| 2. Lanalin wax | 12.0 |
| 3. Candelilla wax | 3.0 |
| 4. Kaolin | 10.0 |
| 5. Castor oil | the rest |
| 6. Dimethylpolysiloxane | 10.0 |
| 7. Trioctanoic ester of glycerin | 2.5 |
| 8. Tabular powder of organic silicone resin (aspect ratio: 19) | 6.0 |
| 9. Titanium oxide | 1.0 |
| 10. Red No. 201 | 1.0 |
| 11. Red No. 202 | 2.0 |
| 12. Blue No. 1 aluminum lake | 0.5 |
| 13. Perfume | proper |

[Making Process]
A: The ingredients 1 to 12 were mixed together under heating to prepare a mixture A.
B: The ingredient 13 was added to the mixture A, and mixed homogeneously therein to prepare a mixture B.
C: The mixture B was filled in capsules to prepare lipstick.

The thus prepared lipstick according to the invention had a lustrous and smooth texture, spread lightly and smoothly, and stayed well due to its good adhesiveness. Thus, the present lipstick can produce a beautiful makeup result, and the result wears well.

EXAMPLE 12

The tabular powder of organic silicone resin prepared in Example 2 was mixed with the following ingredients, and made into a hair rinse in the process described below:

| Ingredients | Amount mixed (%) |
| --- | --- |
| 1. Ethylene glycol distearate | 3.0 |
| 2. Cetanol | 2.0 |
| 3. Propylene glycol monostearate | 3.0 |
| 4. dimethylpolysiloxane (100 cs) | 3.0 |
| 5. Monostearic ester of glycerin | 4.0 |
| 6. Polyoxyethylene (3) stearate | 4.0 |
| 7. Chloroacetyltrimethylammonium | 5.0 |
| 8. Polyoxyethylene (20) cetyl ether | 2.0 |
| 9. Tabular powder of organic silicone resin (aspect ratio: 28) | 2.0 |
| 10. 1,3-Butylene glycol | 5.0 |
| 11. Antiseptic | proper |
| 12. Perfume | proper |
| 13. Purified water | the rest |

[Making Process]
A: The ingredients 1 to 9 were mixed with stirring to prepare a mixture A.
B: The ingredients 10, 11 and 13 were mixed together under heating to prepare a mixture B.
C: The mixture B was added to the mixture A, mixed, cooled, and then mixed with the ingredient 12 to prepare a hair rinse.

The hair rinse thus prepared according to the invention was neither tacky nor heavy, gave fine luster, dry and smooth touch and puff to the hair treated therewith, and made it easy to pass a comb through the hair treated therewith. And these effects lasted a long time.

EXAMPLE 13

The tabular powder of organic silicone resin prepared in Example 3 was mixed with the following ingredients, and made into a hair conditioner in the process described below:

| Ingredients | Amount mixed (%) |
| --- | --- |
| 1. Ethylene glycol distearate | 1.0 |
| 2. Liquid paraffin | 10.0 |
| 3. Squalane | 5.0 |
| 4. Stearyl alcohol | 1.5 |
| 5. Dimethylpolysiloxane | 3.0 |
| 6. Stearic acid | 6.0 |
| 7. Polyoxyethylene (3) stearyl alcohol | 4.5 |
| 8. Polyoxyethylene (150) cetyl ether | 2.0 |
| 9. Tabular powder of organic silicone resin (aspect ratio: 19) | 1.5 |
| 10. 1,3-butylene glycol | 6.0 |
| 11. Antiseptic | proper |
| 12. Perfume | proper |
| 13. Purified water | the rest |

[Making Process]
A: The ingredients 1 to 9 were mixed under heating to prepare a mixture A.
B: The ingredients 10, 11 and 13 were mixed together to prepare a dispersion B.
C: The dispersion B was added to the mixture A, mixed, cooled, and then mixed with the ingredient 12, thereby obtaining a treatment.

The treatment thus prepared according to the invention had neither tacky nor heavy tough, gave fine luster, dry and smooth touch and puff to the hair treated therewith, and made it easy to pass a comb through the hair treated therewith. And these effects lasted a long time.

EXAMPLE 14

The tabular powder of organic silicone resin prepared in Example 3 was mixed with the following ingredients, and made into water-based enamel for manicure in the process described below:

| Ingredients | Amount mixed (%) |
| --- | --- |
| 1. Styrene-acrylic acid copolymer | 40.0 |
| 2. Ethanol | 10.0 |
| 3. Neutralizer | proper |
| 4. carbitol | proper |
| 5. Plasticizer | proper |
| 6. Antifoaming agent | proper |
| 7. Antiseptic | proper |
| 8. Perfume | proper |
| 9. Purified water | the rest |
| 10. Tabular powder of organic silicone resin (aspect ratio: 19) | 1.0 |
| 11. Colored pigment for coloring | 3.0 |

[Making Process]
All ingredients set forth above were mixed homogeneously, and filled in vials.

The thus prepared water-base enamel for manicure was convenient to apply, spread well, had smooth texture and gave a fine luster to nails. The enamel applied kept well. Further, the present water-base enamel hardly caused in its viscosity upon storage, namely it had excellent storage stability.

EXAMPLE 15

The tabular powder of organic silicone resin prepared in Example 2 was mixed with the following ingredients, and made into an aerosol composition in the, process described below:

| Ingredients | Amount mixed (%) |
|---|---|
| 1. Tabular powder of organic silicone resin (aspect ratio: 28) | 3.0 |
| 2. Chloro-hydroxo-aluminum complex | 2.0 |
| 3. Isopropylmethylphenol | 0.3 |
| 4. Sorbitan sesquioleic acid ester | 0.2 |
| 5. Isopropyl myristate | 5.0 |
| 6. Perfume | proper |
| 7. Jetting agent | the rest |

[Making Process]
A: The ingredients 1 to 6 were mixed together to prepare a mixture A.
B: The mixture A was charged in an aerosol can. Then, the can was filled with the ingredient 7.

The aerosol composition thus prepared according to the invention produced a high deodorization effect. The composition was coated in a very thin layer, and the composition coated had neither tacky nor heavy though, and gave a dry and smooth feel. In addition, the present aerosol composition had high re-dispersibility, so it was very usable.

EXAMPLE 16

The milky lotion was prepared using the same ingredients under the same compounding condition:as in Example 5, except that the titanium oxide-incorporated tabular powder of organic silicone resin having an aspect ratio greater than about 1, which was prepared in Example 4, was used in place of the tabular powder of organic silicone resin having an aspect ratio of 32 (which was free of titanium oxide).

The milky lotion obtained had fine appearance similarly to that obtained in Example 5, arouse no uncomfortable feelings, such as rough and tacky feels, in the users when applied to their skin, spread smoothly, caused dry and refreshed feels in the applied skin, and had a very smooth texture.

Further, this milky lotion was stored in a reagent bottle for aging test. Even after 3-month lapse, the lotion had no deposit although it contained the inorganic powder.

COMPARATIVE EXAMPLE 1

The white resin powder prepared by copolymerization reaction according to the same method as in Example 1 was dried, ground with a jet mill, and then put through a sieve. Thus, the organic silicone resin powder having an average particle size of 20 µm was obtained. As to the powder shape, the resin powder obtained was a mixture of globular, columnar, stick-like, tabular and acicular particles.

Another milky lotion was prepared under the same compounding condition as in Example 5, except that the organic silicone resin powder obtained above, was used in place of the tabular powder of organic silicone resin having an aspect ratio of 32. The lotion thus obtained had la dusty gloss and arouse an uncomfortable feeling in users when applied to their skin.

COMPARATIVE EXAMPLE 2

Still another milky lotion was:prepared under the same compounding condition as in Example 5, except that untreated mica was used in place of the tabular powder of organic silicone resin having an aspect ratio of 32.

The thus obtained lotion had a fine appearance, but the aging test by the storage in a reagent bottle showed that it formed a little deposit after the lapse of one week.

Additionally, the foregoing examples are some embodiments of the invention, so that the present invention should not be construed as being limited to those examples. Therefore, any materials are included in the technical scope of the invention if they have in a substantial sense the same constitutions as the technological ideas described in the present claims and the same functions and effects as the present materials.

For instance, although the organic silicone resin powder used as one ingredient of a cosmetic material in each of Examples 5 to 16 is the tabular (aspect ratio: greater than about 1) powder of a copolymer prepared from a radical polymerizable group-containing dimethylorganopolysiloxane and radical polymerizable monomer(s), the same effects are produced even when the copolymer used is a copolymer prepared from compounds having reactive groups other than radical polymerizable groups, e.g., a copolymer of Organopolysiloxane(s) and monomer (s) whose reactive groups are different from each other, such as carboxylic acid group and alcoholic group.

In accordance with the invention, the organic silicone resin is a copolymer prepared by polymerization reaction between an Organopolysiloxane containing one or more of a reactive group and at least one kind of monomer or oligomer capable of reacting to the reactive group, and the powder of such a copolymer is a tabular powder having an aspect ratio greater than about 1. The cosmetic materials containing the present tabular powder as one essential ingredient are non-viscous, arise neither tacky nor heavy feelings in the persons who put them on the skin or the like, spread lightly and smoothly, have good adhesiveness. The skin to which the cosmetic material according to the invention is applied has a dry and smooth texture and acquires a refreshed feel, and these effects last a long time. In other words, the cosmetic materials according to the invention produce a comfortable feeling and excellent results when applied to skin, hair, or so on.

Further, the present organic silicone resin powder has a markedly small specific gravity, compared with inorganic powders so far been used, so that it causes no conventional precipitation trouble.

Furthermore, as the present, organic silicone resin powder has excellent compatibility:with base substances of cosmetics and high dispersibility therein, mixing it as an essential ingredient in cosmetics not only dissolves uncomfortable feels, such as a rough feel which is liable to be caused when conventional organic resin powders are mixed therein and a tacky feel which is liable to be caused when conventional silicone resin powders are mixed therein, but also confer excellent characteristics those conventional resins have by nature, such as stability and a moist texture, on the cosmetics.

Therefore, the combined use of the present organic silicone resin powder and conventional inorganic powders in cosmetics can remarkably improve, the characteristics and handling easiness of the resultant cosmetics, compared with the independent use of inorganic powders in cosmetics, and enables the inexpensive and easy preparation of cosmetics.

What is claimed is:

1. An organic silicone resin powder, having a tabular shape the aspect ratio of which is greater than about 1 and comprising a copolymer produced by polymerization reaction between an organopolysiloxane containing at least one reactive group and at least one monomer or oligomer capable of reacting to said at least one reactive group of said organopolysiloxane, wherein said organopolysiloxane contains at least one amino group, hydroxyl group, epoxy group, carboxylic acid group, radical polymerization group, or combinations thereof, and wherein said at least one monomer or oligomer contains at least one amino group, hydroxyl group, epoxy group, carboxylic acid group, radical polymerization group, or combinations thereof.

2. An organic silicone resin powder according to claim 1, wherein said reacting group is a radical polymerizable group and said monomer or oligomer is a radical polymerizable monomer oligomer.

3. An organic silicone resin powder according to claim 1, further comprising an inorganic powder.

4. An organic silicone resin powder according to claim 2, further comprising an inorganic powder.

5. A method of producing an organic silicone resin powder having a tabular shape the aspect ratio of which is greater than about 1, said method comprising forming a film from a copolymer produced by polymerization reaction between an organopolysiloxane containing at least one reactive group and at least one monomer or oligomer capable of reacting to said reactive group, grinding the film into a powder and putting the powder trough a sieve, wherein said organopolysiloxane contains at least one amino group, hydroxyl group, epoxy group, carboxylic acid group, radical polymerization group, or combinations thereof and wherein said at least one monomer or oligomer contains at least one amino group, hydroxyl group, epoxy group, carboxylic acid group, radical polymerization group, or combinations thereof.

6. A method of producing an organic silicone resin powder in accordance with claim 5, wherein said reacting group is a radical polymerizable group and said monomer or oligomer is a radical polyerizable monomer or oligomer.

7. A method of producing an organic silicone resin powder in accordance with claim 5, wherein said film is formed using a biaxial extruder.

8. A method of producing an organic silicone resin powder in accordance with claim 6, wherein said film is formed using a biaxial extruder.

9. A cosmetic material comprising an organic silicone resin powder according to claim 1.

10. A cosmetic material comprising an organic silicone resin powder according to claim 2.

11. A cosmetic material comprising an organic silicone resin powder according to claim 3.

12. A cosmetic material comprising an organic silicone resin powder according to claim 4.

13. A cosmetic material according to claim 9, wherein the organic silicone resin powder is comprised in a proportion of about 0.01 to about 50% by weight.

14. A cosmetic material according to claim 13, wherein the copolymer has a number average molecular weight of from about 2,000 to about 100,000.

15. A cosmetic material comprising an organic silicone resin powder according to claim 1 and at least one ingredient selected from oils, surfactants or powders.

16. A cosmetic material comprising an organic silicone resin powder according to claim 2 and at least one ingredient selected from oils, surfactants or powders.

17. A cosmetic material comprising an organic silicone resin powder according to claim 3 and at least one ingredient selected from oils, surfactants or powders.

18. A cosmetic material comprising an organic silicone resin powder according to claim 4 and at least one ingredient selected from oils, surfactants or powders.

19. An organic silicone resin powder according to claim 1, wherein said organopolysiloxane contains at least one radical polymerizable group selected from vinyl, styryl, α-methylstyryl, acryl, and methacryl.

20. An organic silicone resin powder according to claim 1, wherein said at least one monomer or oligomer is selected from α-olefins, acrylonitrile, acrylic acid, methacrylic acid, methyl acrylate, methyl methacrylate, butyl acrylate, 2-hydroxyethyl acrylate, 2-hydroxypropyl acrylate, 2-ethylhexyl acrylate, isobornyl acrylate, dicyclopentenyl acrylate, 2-hydroxyethyl methacrylate, N,N-dimethylacrylamide, N-vinylacetamide, N-vinylpyrrolidone, N-vinylcaprolactame, acryloylmorpholine, N-vinylimidazole, maleic anhydride, phenylimide, and oligomers thereof.

21. An organic silicone resin powder according to claim 19, wherein said organopolysiloxane contains at least one radical polymerizable group selected from acryl and methacryl, and said at least monomer or oligomer is selected from α-olefins.

22. An organic silicone resin powder the resin particles of which have a tabular shape, an aspect ratio of greater than about 1, a thickness of 0.1 to 2 μm and an average particle diameter on a volume equivalent basis of 0. 1–100 μm said powder comprising a copolymer produced by polymerization reaction between an organopolysiloxane containing at least one reactive group and at least one monomer or oligomer capable of reacting with said at least one reactive group of said organopolysiloxane, said organopolysiloxane being of the formula $A_xR_ySiO_{(4-x-y)/2}$ wherein A is a reactive group selected from amino, hydroxyl, epoxy, carboxylic acid, a radical polymerizable, and combinations thereof, R is a hydrocarbon group having 1–10 carbon atoms, x is 0.002–1.5, and y is 0–3.0, wherein $1.5 \leq x+y \leq 2.5$, said at least one monomer or oligomer contains at least one amino group, hydroxyl group, epoxy group, carboxylic acid group, radical polymerizable group, or combinations thereof, wherein the ratio of reactive group-containing organopolysiloxanes to reactive monomers or oligomers is 0.1/99.9 to 50/50, and wherein said copolymer has a weight average molecular weight of 2000–100,000 and a grass transition temperature of at least 40° C.

23. An organic silicone resin powder according to claim 1, wherein said resin particles have an aspect ratio of greater than about 1 to 50.

24. An organic silicone resin powder according to claim 1, wherein said resin particles have an aspect ratio of 5 to 50.

25. A method according to claim 5, wherein said resin particles have an aspect ratio of greater than about 1 to 50.

26. A method according to claim 5, wherein said resin particles have an aspect ratio of 5 to 50.

27. An organic silicone resin powder according to claim 22, wherein said resin particles have an aspect ratio of greater than about 1 to 50.

28. An organic silicone resin powder according to claim 22, wherein said resin particles have an aspect ratio of 5 to 50.

29. A cosmetic material according to claim 15, wherein the organic silicone resin powder is present in an amount of 0.01–50% by weight.

30. A cosmetic material according to claim 29, wherein the copolymer has a number, average molecular weight of 2,000–100,000.

31. An organic silicone resin powder according to claim 22, wherein said at least one monomer or oligomer is selected from α-olefins, acrylonitrile, acrylic acid, methacrylic acid, methyl acrylate, methyl methacrylate, butyl acrylate, 2-hydroxyethyl acrylate, 2-hydroxypropyl acrylate, 2-ethylhexyl acrylate, isobomyl acrylate, dicyclopentenyl acrylate, 2-hydroxyethyl methacrylate, N,N-dimethylacrylamide, N-vinylacetamide, N-vinylpyrrolidone, N-vinylcaprolactame, acryloylmorpholine, N-vinylimidazole, maleic anhydride, phenylimide, and oligomers thereof.

32. A method according to claim 5, wherein said organopolysiloxane contains at least one radical polymerizable group selected from vinyl, styryl, α-methylstyryl, acryl, and methacryl.

33. A method according to claim 5, wherein said at least one monomer or oligomer is selected from α-olefins, acrylonitrile, acrylic acid, methacrylic acid, methyl acrylate, methyl methacrylate, butyl acrylate, 2-hydroxyethyl acrylate, 2-hydroxypropyl acrylate, 2-ethylhexyl acrylate, isobomyl acrylate, dicyclopentenyl acrylate, 2-hydroxyethyl methacrylate, N,N-dimethylacrylamide, N-vinylacetamide, N-vinylpyrrolidone, N-vinylcaprolactame, acryloylmorpholine, N-vinylimidazole, maleic anhydride, phenylimide, and oligomers thereof.

* * * * *